US008551003B2

(12) United States Patent
Fukada et al.

(10) Patent No.: US 8,551,003 B2
(45) Date of Patent: Oct. 8, 2013

(54) ULTRASONIC PROBE AND ULTRASONIC DIAGNOSIS DEVICE

(75) Inventors: Makoto Fukada, Tokyo (JP); Shuzo Sano, Tokyo (JP); Akifumi Sako, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 707 days.

(21) Appl. No.: 12/602,119

(22) PCT Filed: May 14, 2008

(86) PCT No.: PCT/JP2008/058821

§ 371 (c)(1), (2), (4) Date: Nov. 27, 2009

(87) PCT Pub. No.: WO2008/146600

PCT Pub. Date: Dec. 4, 2008

(65) Prior Publication Data

US 2010/0154547 A1 Jun. 24, 2010

(30) Foreign Application Priority Data

May 29, 2007 (JP) ................................ 2007-141408

(51) Int. Cl.
*A61B 8/00* (2006.01)

(52) U.S. Cl.
USPC ........... 600/459; 600/437; 600/443; 600/407; 310/311; 310/364; 310/365; 310/366; 310/367; 310/322; 310/334; 438/15; 438/25; 438/26

(58) Field of Classification Search
USPC ......... 600/407, 437, 443, 459; 29/25.35, 594, 29/595, 739, 832, 835, 836; 310/311, 310/364–367, 322, 334; 73/513.34; 438/15, 438/25, 26, 33, 40, 42, 43
See application file for complete search history.

(56) References Cited

U.S. PATENT DOCUMENTS 6,258,034 B1 * 7/2001 Hanafy ......................... 600/459
7,285,897 B2 * 10/2007 Fisher et al. .................. 310/334

(Continued)

FOREIGN PATENT DOCUMENTS

JP 2006-157320 6/2006
JP 2007-125225 5/2007

(Continued)

OTHER PUBLICATIONS

DM Mills, LS Smith. Real-Time in vivo Imaging with Capacitive Micromachined Ultrasound Transducer (cMUT) Linear Arrays. IEEE Ultrasonics Symposium. 2003: 568-571.*

(Continued)

*Primary Examiner* — Unsu Jung
*Assistant Examiner* — Amanda Lauritzen
(74) *Attorney, Agent, or Firm* — Antonelli, Terry, Stout & Kraus, LLP.

(57) ABSTRACT

An ultrasonic probe and an ultrasonic diagnosis device which can improve electrical safety for an operator are provided. The ultrasonic probe 2 has an insulating portion 62 between a mounting board 43 and a case 25. Since electrical leakage from the internal device of the ultrasonic probe 2 can be prevented, electrical safety of the ultrasonic probe 2 for the operator can be improved. A conductive film 61 is provided on the ultrasonic wave radiation side of a cMUT chip 20, and a conductive member 63 is provided along the insulating member 62. A conductive film 61 and a conductive member 63 are connected by a conductive member 64. A closed space having a ground potential is formed by the conductive film 61, the conductive member 63 and a coaxial cable 55 connected to ground. Main components or the body circuits of the ultrasonic probe 2 are contained in the closed space having the ground potential and shielded electrically from the outside.

13 Claims, 11 Drawing Sheets

(56) References Cited

U.S. PATENT DOCUMENTS

| | | | | |
|---|---|---|---|---|
| 7,449,821 | B2 * | 11/2008 | Dausch | 310/364 |
| 7,808,157 | B2 * | 10/2010 | Oakley et al. | 310/334 |
| 2010/0168583 | A1 * | 7/2010 | Dausch et al. | 600/466 |

FOREIGN PATENT DOCUMENTS

| | | | |
|---|---|---|---|
| WO | WO 2006/030793 | A1 | 3/2006 |
| WO | WO 2007/058056 | A1 | 5/2007 |
| WO | WO 2008/056643 | A1 | 5/2008 |

OTHER PUBLICATIONS

YHuang, E Haeggstrom, B Bayram, X Zhuang, AS Ergun, CH Cheng, BT Khuri-Yakub. Collapsed Regime Operation of Capacitive Micromachined Ultrasonic Transducers based on Wafer-Bonding Technique. IEEE Ultrasonics Symposium. 2003: 1161-1164.*

* cited by examiner (b) CROSS-SECTIONAL VIEW OF LINE F-F (a) CROSS-SECTIONAL VIEW OF LINE G-G CROSS-SECTIONAL VIEW OF LINE H-H
(a)

CROSS-SECTIONAL VIEW OF LINE I-I
(b)

ULTRASONIC PROBE AND ULTRASONIC DIAGNOSIS DEVICE

CROSS-REFERENCE TO RELATED APPLICATIONS

This application is a 35 U.S.C. §371 national stage entry of PCT/JP2008/058821, filed May 14, 2008, which claims foreign priority to Japanese patent application 2007-141408, filed May 29, 2007.

TECHNICAL FIELD

The present invention relates to an ultrasonic probe and an ultrasonic diagnosis device for photographing a diagnosis image.

BACKGROUND ART

An ultrasonic diagnosis device is a device for photographing a diagnosis image based on a reflection echo signal output from an ultrasonic probe. In the ultrasonic probe, a plurality of ultrasonic vibrators is arranged. The ultrasonic vibrator converts a driving signal into an ultrasonic wave, transmits the ultrasonic wave to a subject, and receives and converts a reflection echo signal generated from the subject into an electrical signal.

Recently, an ultrasonic probe using a Capacitive Micromachined Ultrasonic Transducer (cMUT) has been developed. The cMUT is a superfine capacitive ultrasonic vibrator manufactured by a semiconductor micromachining process. In addition, an ultrasonic probe which is capable of reducing manufacturing cost and improving image quality by manufacturing a vibrator cell by a semiconductor manufacturing process using a board of an inorganic material, forming a base plate of a resin material in the vibrator cell, and removing the board of the inorganic material is suggested (see Patent Document 1).

Patent Document 1: Japanese Unexamined Patent Application Publication No. 2006-157320

DISCLOSURE OF THE INVENTION

Problem that the Invention is to Solve

However, in the conventional ultrasonic probe, an insulating structure is insufficient and safety is hard to secure with respect to an operator and a subject.

In the cMUT probe, a DC voltage is applied to a lower electrode as a bias voltage with respect to a silicon board of the cMUT and an AC high-frequency voltage is applied to an upper electrode as a driving signal with respect to the lower electrode. As a result, the upper electrode is not a ground layer having a ground potential. In the conventional cMUT probe, electrical leakage from the cMUT chip may be generated and the electrical safety for an operator who operates the cMUT probe while grasping a casing portion (case) is insufficient.

The present invention is contrived to solve the above-mentioned problems. An object of the present invention is to provide an ultrasonic probe and an ultrasonic diagnosis device capable of improving electrical safety for an operator.

Means for Solving the Problem

In order to achieve the above-mentioned object, according to a first invention, there is provided an ultrasonic probe including: a Capacitive Micromachined Ultrasonic Transducer (cMUT) chip having a plurality of vibration elements to transmit or receive an ultrasonic wave; a mounting board on which electrical parts for controlling the vibration elements are mounted; an electrical wiring portion to connect the mounting board and the cMUT chip; and a casing portion for storing the cMUT chip, the mounting board and the electrical wiring portion, wherein an insulating portion is provided between the mounting board and the casing portion.

In the ultrasonic probe of the first invention, the insulating layer is provided between the mounting board and the casing portion such as a case. The insulating layer is provided on the surface of the electrical wiring portion or the inner surface of the casing portion. The electrical wiring portion is a flexible printed circuit connected to the cMUT chip. The electrical parts such as an electronic circuit, a resistor or a capacitor are mounted on the mounting board.

By providing the insulating layer between the mounting board and the casing portion, since electrical leakage from an internal device of the ultrasonic probe is prevented, it is possible to improve electrical safety of the ultrasonic probe for an operator.

It is preferable that the cMUT chip, the electrical wiring portion and the mounting board are stored in a closed space formed by a ground layer having a ground potential. The ground layer is a conductive film formed on an ultrasonic wave radiation side of the cMUT chip, a conductive member provided along a surface of the electrical wiring portion or a conductive film formed along an inner surface of the casing portion. The conductive members or the conductive films are electrically connected so as to be connected to ground on the body side of the ultrasonic diagnosis device.

Accordingly, since the main components or the body circuits of the ultrasonic probe are contained in a closed space having a ground potential so as to be electrically shielded from the outside, it is possible to prevent influence of an electromagnetic wave from the inside to the outside or from the outside to the inside. In addition, it is possible to improve electrical safety of the ultrasonic probe for the operator.

In addition, a filler may be filled in a portion or all of the internal space of the casing portion. By filling the filler in the overall internal space of the casing portion, it is possible to prevent corrosion of the internal constituent member. In addition, it is possible to improve impact resistance or an insulating property and to improve safety of the ultrasonic probe. In addition, it is possible to prevent deformation or damage of the ultrasonic probe.

According to a second invention, there is provided an ultrasonic diagnosis device including the ultrasonic probe according to the first invention.

Advantage of the Invention

By providing an insulating portion between a mounting board and a casing portion, since electrical leakage from an internal device of an ultrasonic probe is prevented, it is possible to improve electrical safety of the ultrasonic probe for an operator.

DESCRIPTION OF REFERENCE NUMERALS AND SIGNS

Figure 1:
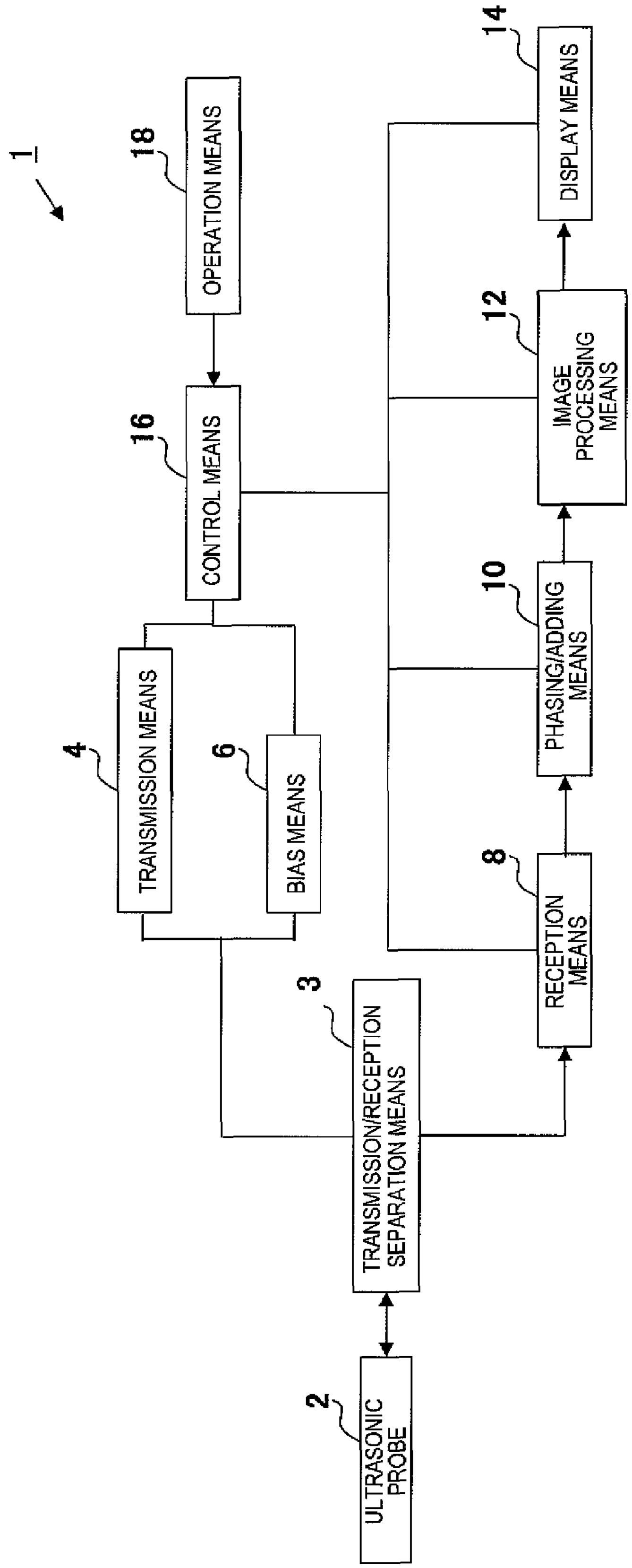
FIG. 1 is a view showing the configuration of an ultrasonic diagnosis device 1.

1: Ultrasonic diagnosis device, 2, 2*a*, 2*b*: ultrasonic probe, 3: transmission/reception separation means, 4: transmission means, 6: bias means, 8: reception means, 10: phasing/adding means, 12: image processing means, 14: display means, 16: control means, 18: operation means, 20: cMUT chip, 21-1, 21-2: vibrator, 22: vibration element, 23: backing layer, 25: case, 26: acoustic lens, 27: lower electrode, 28: upper electrode, 41: flexible printed circuit (bias), 42: flexible printed circuit (signal), 43: mounting board, 44: cable, 45, 46: terminal, 47, 48: wire, 51, 52, 53: connector, 54: electrical part, 55: coaxial cable (shield line), 57: coaxial cable (bias), 58: coaxial cable (signal), 60, 65, 69: sealant, 61: conductive film, 62: insulating member, 62*a*: insulating film, 63: conductive member, 63*a*: conductive film, 64, 64*a*: conductive member, 66, 66*b*: filler, 70: connector, 102, 107: ground Best Mode For Carrying Out The Invention Hereinafter, an ultrasonic probe and an ultrasonic diagnosis device according to an embodiment of the present invention will be described in detail with reference to the accompanying drawings. In addition, in the following description and the accompanying drawings, components having substantially the same function are denoted by the same reference numerals and repetition of the description will be omitted.

(1. Configuration of Ultrasonic Diagnosis Device)

First, the configuration of the ultrasonic diagnosis device 1 will be described with reference to FIG. 1.

FIG. 1 is a view showing the configuration of the ultrasonic diagnosis device 1.

The ultrasonic diagnosis device 1 includes an ultrasonic probe 2, transmission/reception separation means 3, transmission means 4, bias means 6, reception means 8, phasing/adding means 10, image processing means 12, display means 14, control means 16, and operation means 18.

The ultrasonic probe 2 is a device which is brought into contact with a subject so as to transmit or receive an ultrasonic wave to or from the subject. The ultrasonic wave is emitted from the ultrasonic probe 2 to the subject, and a reflection echo signal generated from the subject is received by the ultrasonic probe 2.

The transmission means 4 is a device for supplying an AC high-frequency voltage as a driving signal.

The bias means 6 is a device for applying a DC voltage as a bias voltage.

The reception means 8 is a device for receiving the reflection echo signal output from the ultrasonic probe 2. The reception means 8 also performs an analog-to-digital converting process with respect to the received reflection echo signal.

The transmission/reception separation means 3 switches and separates transmission and reception such that the driving signal is sent from the transmission means 4 to the ultrasonic probe 2 at the time of transmission and the reception signal is sent from the ultrasonic probe 2 to the reception means 8 at the time of reception.

The phasing/adding means 10 is a device for phasing and adding the received reflection echo signal.

The image processing means 12 is a device for configuring a diagnosis image (for example, a tomographic image or a blood stream image) based on the phased added reflection echo signal.

The display means 14 is a display device for displaying the image-processed diagnosis image.

The control means 16 is a device for controlling the above-described components.

The operation means 18 is a device for providing an instruction to the control means 16. The operation means 18 is, for example, an input device such as a track ball, a keyboard, a mouse or the like.

(2. Ultrasonic Probe 2)

Next, the ultrasonic probe 2 will be described with reference to FIGS. 2 to 4.

(2-1. Configuration of Ultrasonic Probe 2)

Figure 2:
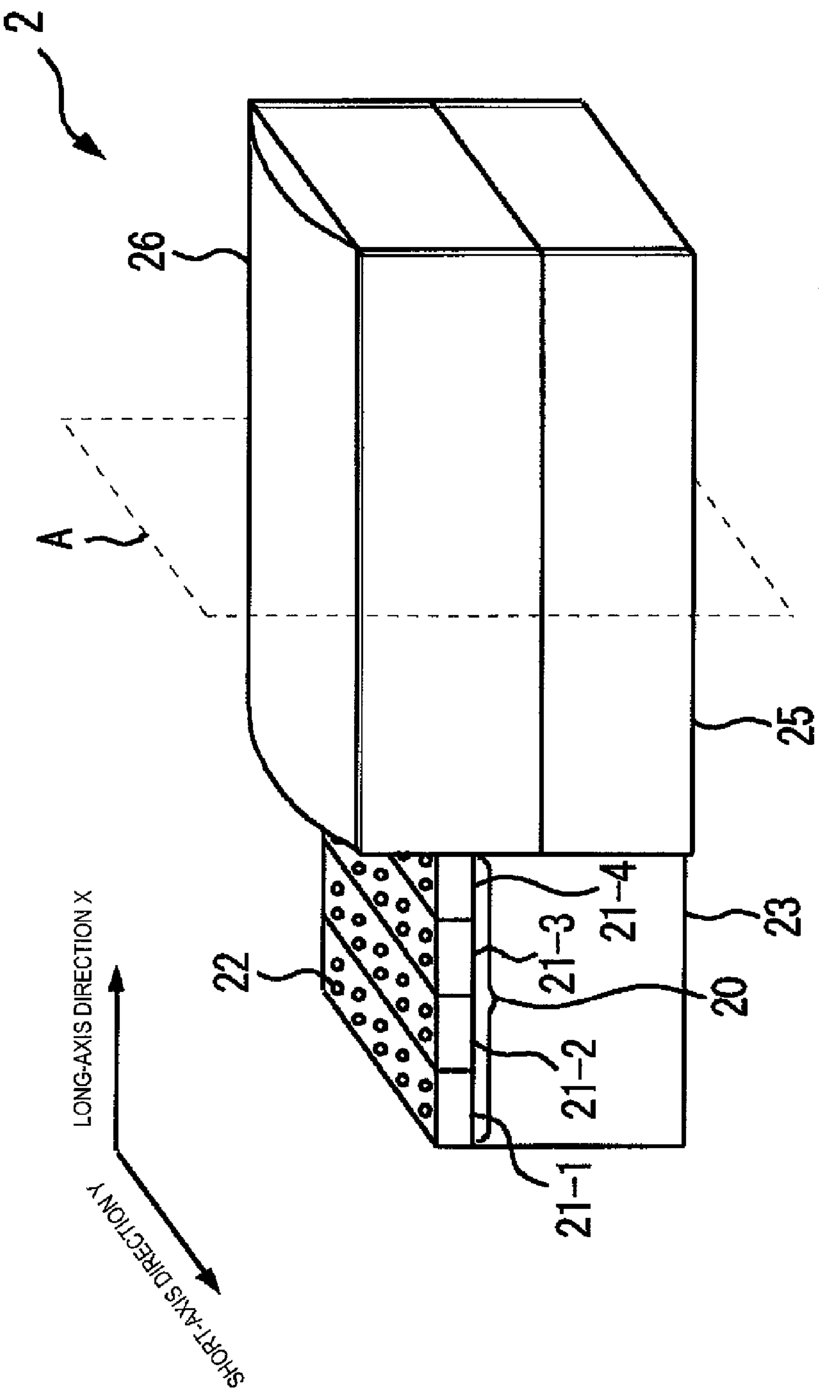
FIG. 2 is a view showing the configuration of an ultrasonic probe 2.

FIG. 2 is a view showing the configuration of the ultrasonic probe 2. FIG. 2 is a partial cutout perspective view of the ultrasonic probe 2.

The ultrasonic probe 2 has a cMUT chip 20. The cMUT chip 20 is a one-dimensional array type vibrator group in which a plurality of vibrators 21-1, vibrators 21-2, . . . is arranged in a stripe shape. A plurality of vibration elements 22 is arranged in the vibrators 21-1, the vibrators 21-2, . . . . In addition, a vibration group having another shape, such as a two-dimensional array type or convex type vibration group, may be used.

A backing layer 23 is provided on a rear surface side of the cMUT chip 20. An acoustic lens 26 is provided on an ultrasonic wave emission side of the cMUT chip 20. The cMUT chip 20 and the backing layer 23 are received in a case 25.

The cMUT chip 20 generates and transmits an ultrasonic wave to the subject based on the driving signal from the transmission means 4 and the bias voltage from the bias means 6. The reception means 8 converts the ultrasonic wave generated from the subject into an electrical signal and receives the electrical signal as the reflection echo signal.

The backing layer 23 absorbs the propagation of the ultrasonic wave emitted from the cMUT chip 20 to the rear surface side so as to suppress excessive vibration.

The acoustic lens 26 is a lens for converging an ultrasonic beam transmitted from the cMUT chip 20. The curvature of the acoustic lens 26 is determined based on one focal length.

In addition, a matching layer may be provided between the acoustic lens 26 and the cMUT chip 20. The matching layer is a layer for matching acoustic impedance of the cMUT chip 20 and the subject so as to improve transmission efficiency of the ultrasonic wave.

(2-2. Vibrator 21)

Figure 3:
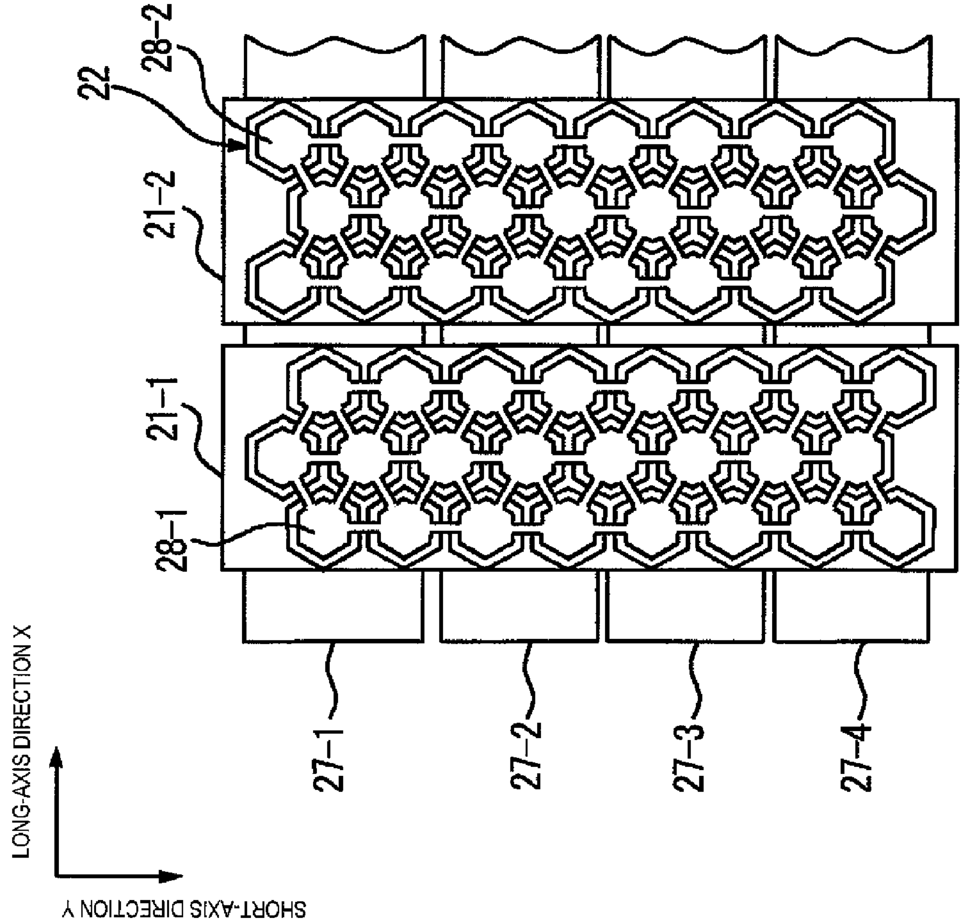
FIG. 3 is a view showing a vibrator 21.

FIG. 3 is a view showing the configuration of the vibrator 21.

Upper electrodes 28 of the vibration element 22 are connected for each of the vibrators 21 divided in a long-axis direction X. That is, an upper electrode 28-1, an upper electrode 28-2, . . . are arranged in parallel in the long-axis direction X. Lower electrodes 27 of the vibration element 22 are connected for each of sections divided in a short-axis direction Y. That is, a lower electrode 27-1, a lower electrode 27-2, . . . are arranged in parallel in the short-axis direction Y.

(2-3. Vibration Element 22)

Figure 4:
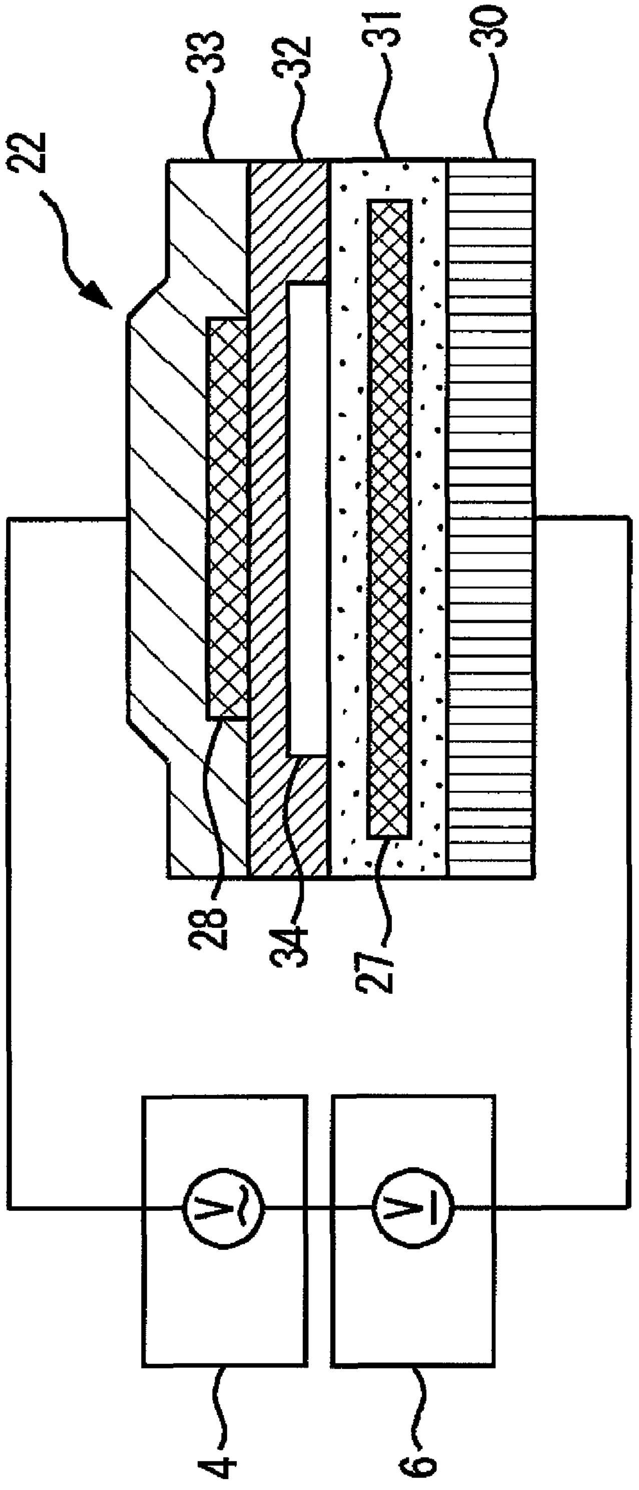
FIG. 4 is a view showing the configuration of a vibration element 22.

FIG. 4 is a view showing the configuration of the vibration element 22. FIG. 4 is a cross-sectional view of one vibration element 22. The vibration element 22 includes a board 30, a film body 31, a frame body 32, a film body 33, the upper electrode 28 and the lower electrode 27. The vibration element 22 is formed by micromachining according to a semiconductor process. In addition, the vibration element 22 corresponds to one element of the cMUT.

The board 30 is a semiconductor board such as a silicon board.

The film body 33 and the frame body 32 are formed of a semiconductor compound such as a silicon compound. The film body 33 is provided on the ultrasonic wave emission side of the frame body 32. The upper electrode 28 is provided between the film body 33 and the frame body 32. The lower electrode 27 is provided in the film body 31 formed on the board 30. An internal space 34 partitioned by the frame body 32 and the film body 31 is in a vacuum state or is filled with predetermined gas.

The upper electrode 28 and the lower electrode 27 are connected to the transmission means 4 and the bias means 6, respectively.

When the ultrasonic wave is transmitted, the DC bias voltage Va is applied to the vibration element 22 through the upper electrode 28 and the lower electrode 27 and an electrical field is generated by the bias voltage Va. The film body 33 is tensioned by the generated electrical field to obtain a predetermined electromechanical coupling coefficient Sa. When the driving signal is supplied from the transmission means 4 to the upper electrode 28, the ultrasonic wave is emitted from the film body 33 based on the electromechanical coupling coefficient Sa.

In addition, when the DC bias voltage Vb is applied to the vibration element 22 through the upper electrode 28 and the lower electrode 27, an electrical field is generated by the bias voltage Vb. The film body 33 is tensioned by the generated electrical field to obtain a predetermined electromechanical coupling coefficient Sb. When the driving signal is supplied from the transmission means 4 to the upper electrode 28, the ultrasonic wave is emitted from the film body 33 based on the electromechanical coupling coefficient Sb.

Here, if the bias voltage is "Va<Vb", the electromechanical coupling coefficient becomes "Sa<Sb".

Meanwhile, if the ultrasonic wave is received, the film body 33 is excited by the reflection echo signal generated from the subject such that the capacitance of the internal space 34 is changed. Based on a change in capacitance of the internal space 34, the electrical signal is detected through the upper electrode 28.

The electromechanical coupling coefficient of the vibration element 22 is determined by a tension degree of the film body 33. Accordingly, if the tension degree of the film body 33 is controlled by changing the level of the bias voltage applied to the vibration element 22, it is possible to change sound pressure (for example, amplitude) of the ultrasonic wave emitted from the vibration element 22 even when the driving signal having the same amplitude is input.

(3. First Embodiment)

Next, a first embodiment will be described with reference to FIGS. 5 to 8.

(3-1. Constituent Member of Ultrasonic Probe 2)

Figure 5:
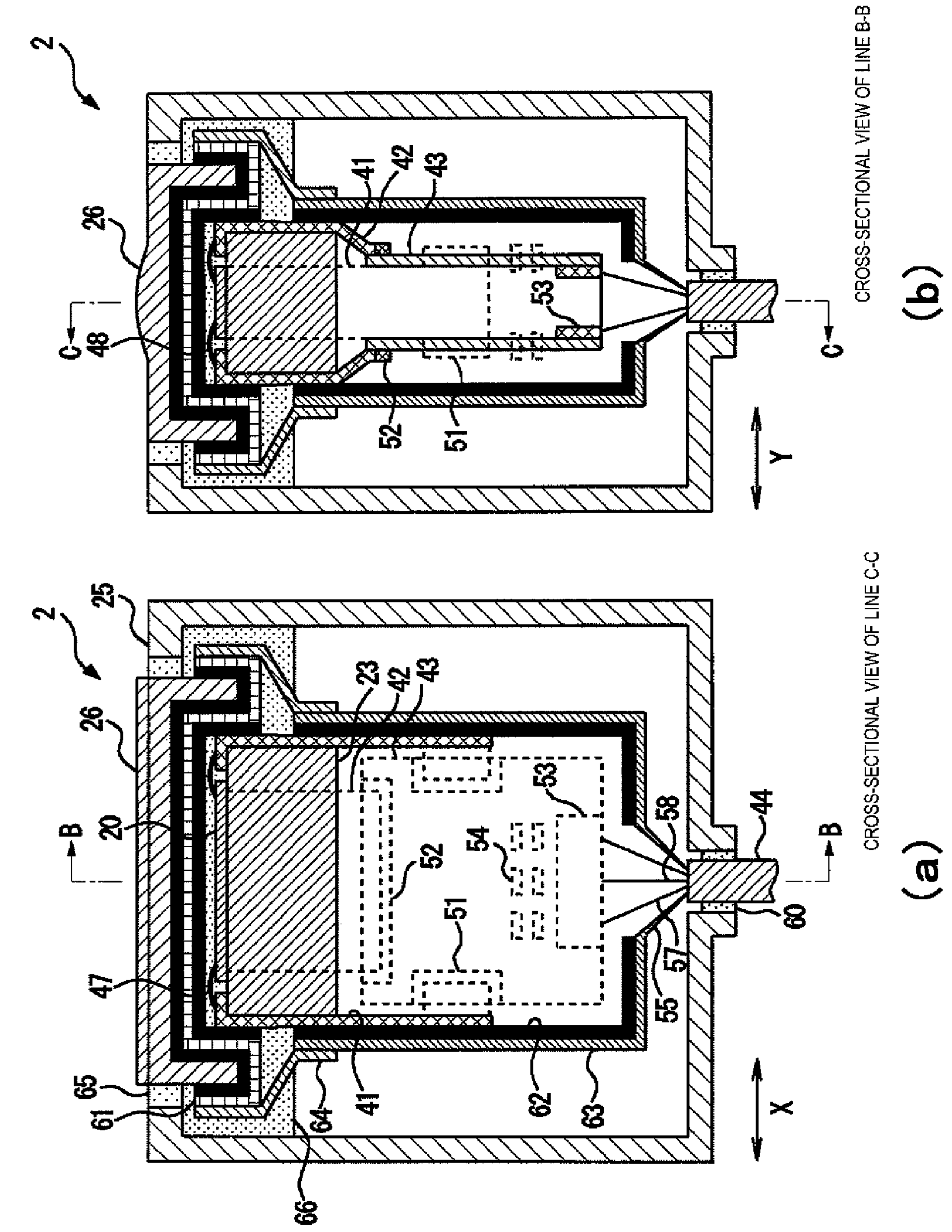
FIG. 5 is a view showing the ultrasonic probe 2 according to a first embodiment.

FIG. 5 is a view showing the ultrasonic probe 2 according to a first embodiment. FIG. 5(*a*) is a cross-sectional view of a long-axis direction X. FIG. 5(*b*) is a cross-sectional view of a short-axis direction Y. FIG. 5(*a*) is a cross-sectional view of line C-C of FIG. 5(*b*), and FIG. 5(*b*) is a cross-sectional view of line B-B of FIG. 5(*a*). FIG. 5(*b*) corresponds to a cross-sectional view of a plane A of the ultrasonic probe 2 of FIG. 2.

The ultrasonic probe 2 is connected to the body of the ultrasonic diagnosis device 1 through a cable 44. The acoustic lens 26 is provided on the ultrasonic wave emission side of the cMUT chip 20. As the material of the acoustic lens 26, for example, silicon rubber is used. The backing layer 23 is adhered on the rear surface side of the cMUT chip 20. A Flexible Printed Circuit (FPC) 41 and a FPC 42 are provided along the upper surface periphery and the four side surfaces of the backing layer 23. The FPC 41 and the FPC 42 are adhered to the upper surface periphery of the backing layer 23 in the short-axis direction Y and the long-axis direction X.

The FPC 41 and the FPC 42 are connected to the mounting board 43 through a connector 51 and a connector 52, respectively. A conducting circuit between each of the terminals of the FPC 41 and the FPC 42 and the cable 44 is provided on the mounting board 43. An electrical part 54 for controlling the vibration element 22, such as a resistor or a capacitor, is mounted on the mounting board 43.

The wiring (bias) from the FPC 41 is connected to a coaxial cable 57 through a connector 53 of the mounting board 43. The wiring (signal) from the FPC 42 is connected to a coaxial cable 58 through the connector 53 of the mounting board 43.

A conductive film 61 is formed along an inner surface and an outer surface of the acoustic lens 26. The conductive film 61 is, for example, a Cu film formed by deposition. In addition, an insulating film may be formed together with the conductive film 61. Two insulating films may be formed with the conductive film 61 interposed therebetween.

An insulating member 62 and a conductive member 63 are provided along the surface of the FPC 41 and the FPC 42. The insulating member 62 is a member having an insulating property. The insulating member is, for example, an insulating tape formed of silicon oxide or paraxylylene. The conductive member 63 is a member having conductivity. The conductive member 63 is, for example, a Cu tape.

The conductive film 61 and the conductive member 63 are connected through a conductive member 64. The conductive member 64 is a high-reliable high-rigidity conductive member which is hard to damage compared with the conductive film 61. The conductive member 64 is, for example, a Cu tape. The conductive member 64 is fixed to the conductive film 61 of the outer side surface of the acoustic lens 26 and the conductive member 63 provided on the surface of the FPC 41 or the FPC 42.

The conductive member 63 is connected to a coaxial cable 55 (shield line). The coaxial cable 55, the coaxial cable 57 and the coaxial cable 58 are bundled by the cable 44 so as to be connected to the body of the ultrasonic diagnosis device 1.

The case 25 is provided on the four surface side of the ultrasonic probe 2. The case 25 is fixed to the four surface side of the acoustic lens 26. An operator grasps the case 25 and operates the ultrasonic probe 2. A sealant 65 is filled in a gap between the case 25 and the acoustic lens 26. A sealant 60 is filled in a gap between the case 25 and the cable 44. In addition, a filler 66 is filled between the acoustic lens 26 and the case 25.

In addition, it is preferable that the upper end of the case 25 is located above the cMUT chip 20. Accordingly, even when an unexpected state such as falling of the ultrasonic probe 2 occurs, it is possible to prevent direct impact so as to protect the cMUT chip 20.

(3-2. Wiring of Ultrasonic Probe 2)

Figure 6:
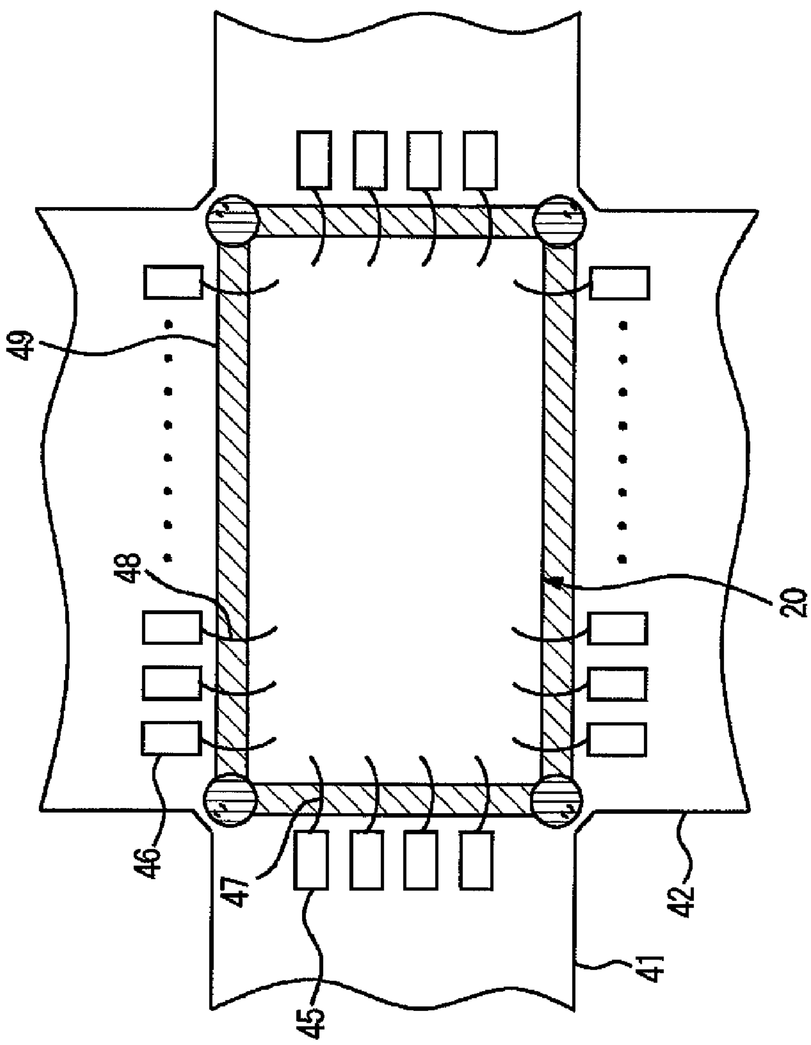
FIG. 6 is a view showing electrical connection between a FPC and a cMUT chip.

FIG. 6 is a view showing electrical connection between the FPC and the cMUT chip.

The FPC 41, the FPC 42 and the cMUT chip 20 are electrically connected through a wire 47 and a wire 48, respectively. The wire 47 and the wire 48 are connected by a wire bonding method. An Au wire or the like may be used as the wire 47 and the wire 48.

In the upper surface periphery of the cMUT chip 20, the lower electrode 27 of the cMUT chip 20 and a terminal 45 of the FPC 41 are connected by the wire 47, and the upper electrode 28 of the cMUT chip 20 and a terminal 46 of the FPC 42 are connected by the wire 48. A photo-curable resin 49 is filled in the periphery of the wire 47 and the wire 48 such that a connection portion is sealed.

(3-3. Connector)

Figure 7:
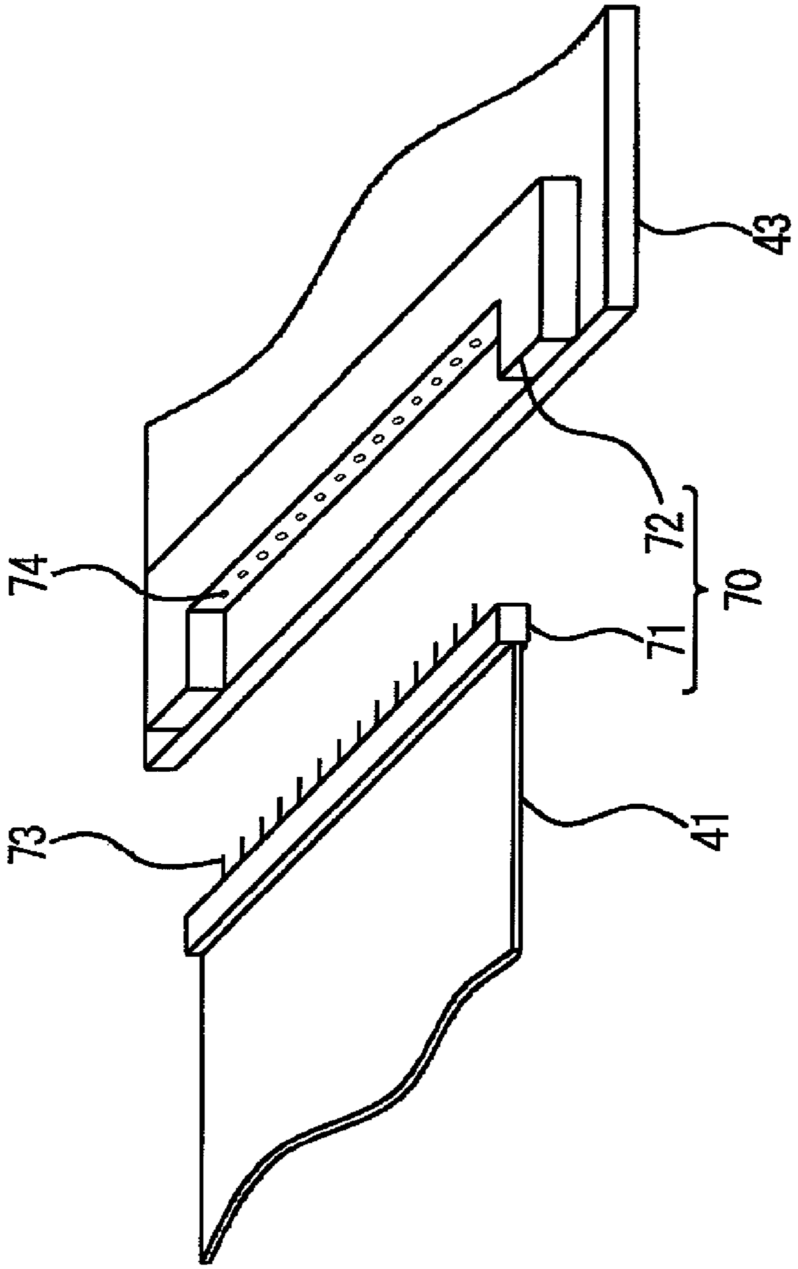
FIG. 7 is a view showing a connector 70 used for connection with a mounting board 43.

FIG. 7 is a view showing a connector 70 used for connection with the mounting board 43.

A connector 70 includes a pin connector 71 and a socket 72. The pin connector 71 is provided on an end of the ETC 41. Pins 73 which are protrusion-shaped electrodes are provided on the pin connector 71. The socket 72 is provided on an end of the mounting board 43. Holes 74 corresponding to the pins 73 are provided in the socket 72. The pin connector 71 is fitted into the socket 72 such that the pins 73 are inserted into the holes 74, thereby electrically connecting the FPC 41 and the mounting board 43.

In addition, the connector 70 of FIG. 7 may be used as the connector 51, the connector 52 and the connector 53 of FIG. 5, and another connector may be used if connection with the mounting board 43 is possible. For example, a connector in which a terminal exposed from the end of the FPC 41 or the FPC 42 is directly inserted into the socket of the mounting board 43 may be used.

(3-4. Connection of Ultrasonic Probe 2 and Body of Ultrasonic Diagnosis Device 1)

Figure 8:
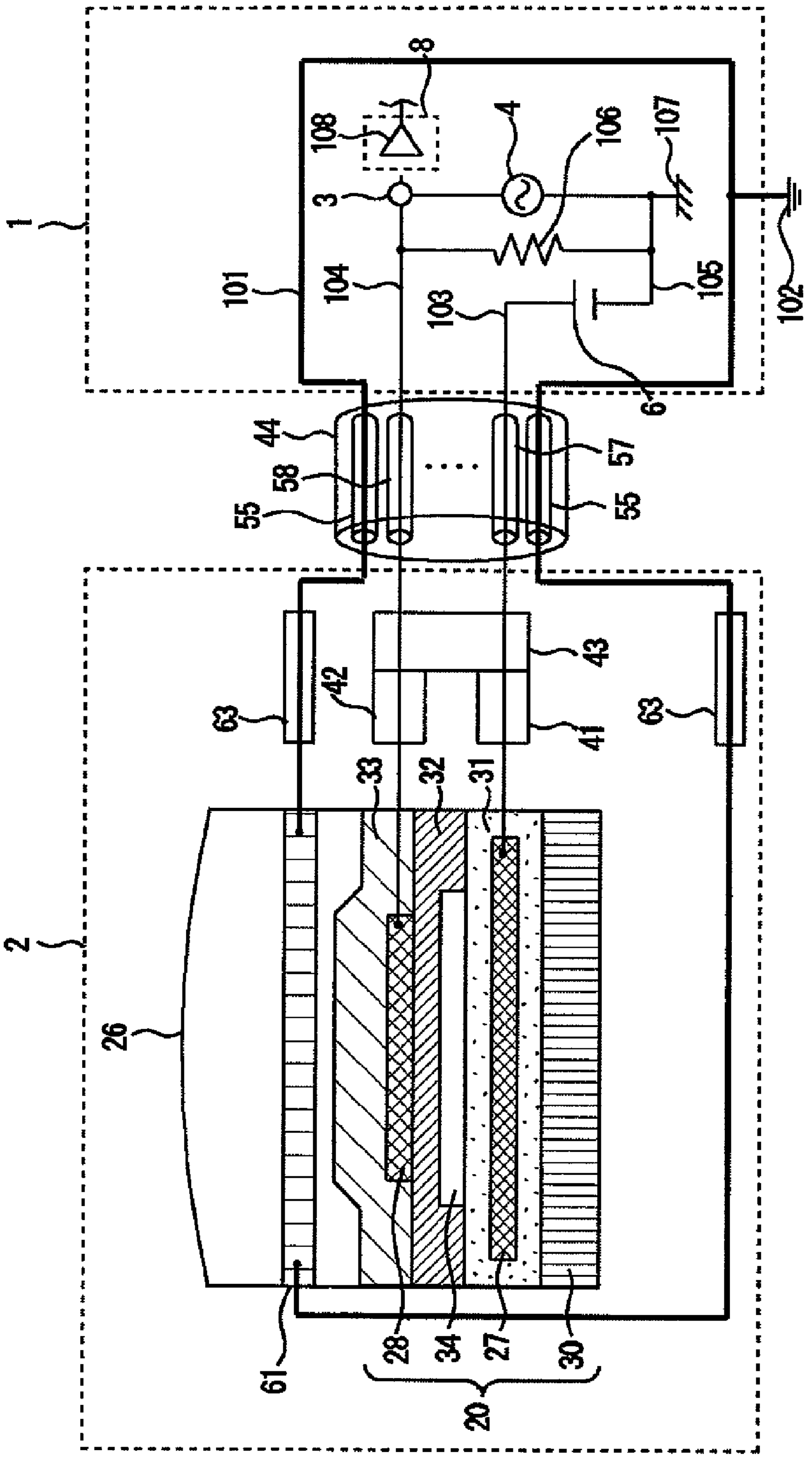
FIG. 8 is a schematic view showing electrical connection between the ultrasonic probe 2 and the body of the ultrasonic diagnosis device 1.

FIG. 8 is a schematic view showing electrical connection between the ultrasonic probe 2 and the body of the ultrasonic diagnosis device 1. The ultrasonic probe 2 and the body of the ultrasonic diagnosis device 1 are connected through the cable 44. The cable 44 has the plurality of coaxial cable 55, coaxial cable 57 and coaxial cable 58.

The lower electrode 27 of the cMUT chip 20 is connected to the coaxial cable 57 through the FPC 41 and the mounting board 43. The coaxial cable 57 is connected to a wiring 103 in the body of the ultrasonic diagnosis device 1. The wiring 103 is connected to the bias means 6. The number of coaxial cables 57 is equal to the number of lower electrodes 27 which are commonly placed in the cMUT chip 20.

The upper electrode 28 of the cMUT chip 20 is connected to the coaxial cable 58 through the FPC 42 and the mounting board 43. The coaxial cable 58 is connected to a wiring 104 in the body of the ultrasonic diagnosis device 1. The wiring 104 is connected to a reception amplifier 108 and the transmission means 4 in the reception means 8 through the transmission/reception separation means 3. The number of coaxial cables 58 is equal to the number of upper electrodes 28 which are commonly placed in the cMUT chip 20.

A resistor 106 is placed between the wiring 104 and the wiring 105. The wiring 105 is connected to ground 107. The resistor 106 is a resistor element for stabilizing the DC potential of the upper electrode 28 to a ground potential. Bias means 6 is placed between the wiring 103 and the wiring 105. The bias means 6 generates a potential difference between the upper electrode 28 and the lower electrode 27. The transmission means 4 applies an AC high-frequency voltage to the upper electrode 28 as the driving signal. In detail, the upper electrode 28 becomes DC=ground (reference potential (0)) and AC=Vpp and the lower electrode 27 becomes DC=Vdc and AC=0.

The conductive film 61 of the ultrasonic probe 2 is connected to the coaxial cable 55 through the conductive member 63. The conductive member 63 is formed so as to cover the internal devices (the FPC 41, the FPC 42 and the mounting board 43) of the ultrasonic probe 2. The conductive member 63 is connected to the wiring 101 in the body of the ultrasonic diagnosis device 1 through the coaxial cable 55. The wiring 101 is formed so as to cover the internal circuit (the wiring 104, the wiring 103, the resistor 106 or the like) in the body of the ultrasonic diagnosis device 1. The wiring 101 is connected to ground 102. In detail, in the conductive film 61, the conductive member 63, the coaxial cable 55 and the wiring 101, DC=ground (reference potential (0)) and AC=0.

The conductive film 61, the conductive member 63, the coaxial cable 55, the wiring 101 and ground 102 form a protective circuit. This protective circuit prevents an external electromagnetic wave from entering the body of the ultrasonic diagnosis device 1 and the internal circuit of the ultrasonic probe 2 and prevents electricity generated in the body of the ultrasonic diagnosis device 1 and the ultrasonic probe 2 from being discharged to the outside.

(3-5. Effect of First Embodiment)

In the ultrasonic probe 2 of the first embodiment, the insulating member 62 is provided between the case 25 and the ultrasonic probe along the FPC 41 and the FPC 42. Since electrical leakage from the internal device of the ultrasonic probe 2 is prevented, it is possible to improve electrical safety of the ultrasonic probe 2 for the operator.

In addition, it is preferable that a material having a high insulating property and excellent heat resistance is used as the insulating member 62. For example, a tape material or a sheet material having excellent insulating property and heat resistance, such as kapton tape, TEFLON (registered trademark) material, vinyl chloride resin, polyurethane, polyethylene or the like, is used as the insulating member 62.

In the ultrasonic probe 2, a closed space having a ground potential is formed by the conductive film 61, the conductive member 63, the coaxial cable 55, the wiring 101 of the body device and ground 102. That is, since the main components or the body circuits of the ultrasonic probe 2 are contained in the closed space having the ground potential, it is possible to prevent the influence due to the unnecessary external wave or to prevent an external device from being adversely affected by the electromagnetic wave generated by the ultrasonic probe 2. Even when the case 25 is damaged, the ground potential of the conductive member 63 prevents an electric shock thus improving the electrical safety of the ultrasonic probe for the operator.

In addition, the conductive film 61 is provided on the ultrasonic wave radiation side of the cMUT chip 20 as a ground layer. Accordingly, even when the acoustic lens 26 is damaged, the ground potential of the conductive film 61 prevents an electric shock thus improving the electrical safety of the ultrasonic probe for the operator.

(4. Second Embodiment)

Next, a second embodiment will be described with reference to FIG. 9.

Figure 9:
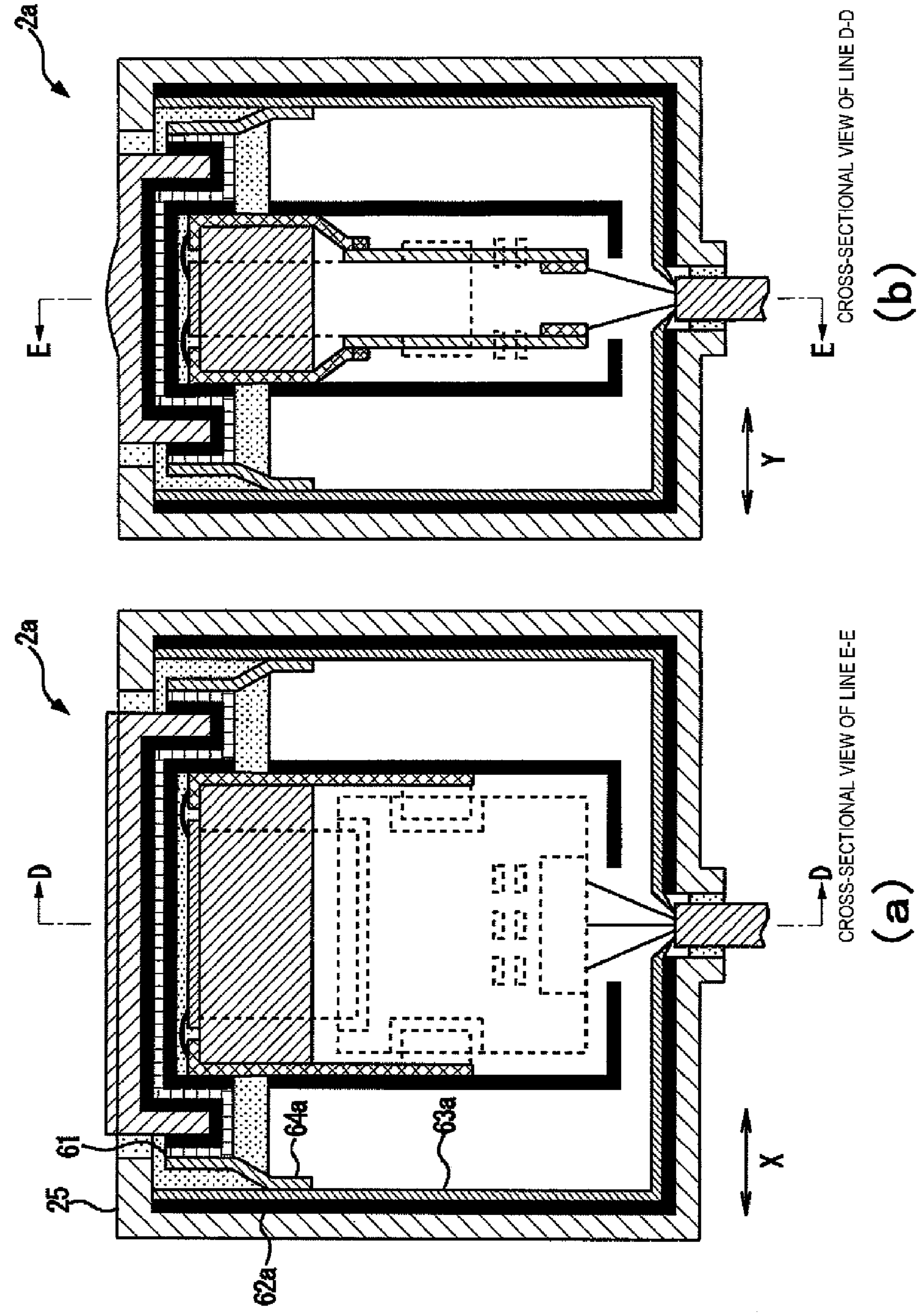
FIG. 9 is a view showing an ultrasonic probe 2*a* according to a second embodiment.

FIG. 9 is a view showing an ultrasonic probe 2*a* according to the second embodiment. FIG. 9(*a*) is a cross-sectional view of a long-axis direction X. FIG. 9(*b*) is a cross-sectional view of a short-axis direction Y. FIG. 9(*a*) is a cross-sectional view of line E-E of FIG. 9(*b*), and FIG. 9(*b*) is a cross-sectional view of line D-D of FIG. 9(*a*). FIG. 9(*b*) corresponds to a cross-sectional view of a plane A of the ultrasonic probe 2 of FIG. 2.

Although the conductive member 63 is provided along the surface of the FPC 41 and the FPC 42 in the first embodiment, a conductive film 63*a* is formed along an inner surface of the case 25 in the second embodiment.

The conductive film 61 and the conductive film 63*a* are connected through a conductive member 64*a*. The conductive member 64*a* of FIG. 9 is equal to the conductive member 64 of FIG. 5. The conductive member 64*a* is fixed to the conductive film 61 of the outer side surface of the acoustic lens 26 and the conductive film 63*a* formed on the inner surface of the case 25.

In the ultrasonic probe 2*a* of the second embodiment, an insulating member 62*a* is provided along the inner surface of the case 25. Similar to the first embodiment, since electrical leakage from the internal device of the ultrasonic probe 2*a* is prevented, it is possible to improve electrical safety of the ultrasonic probe 2*a* for the operator.

In addition, in the ultrasonic probe 2*a*, since the conductive film 63*a* is formed along the inner surface of the case 25, the main components or the body circuits of the ultrasonic probe 2*a* are contained in the closed space having the ground potential similar to the first embodiment. Accordingly, it is possible to prevent influence due to an unnecessary external wave or prevent an external device from being adversely affected by the electromagnetic wave generated by the ultrasonic probe 2*a*.

(5. Third Embodiment)

Next, a third embodiment will be described with reference to FIG. 10.

Figure 10:
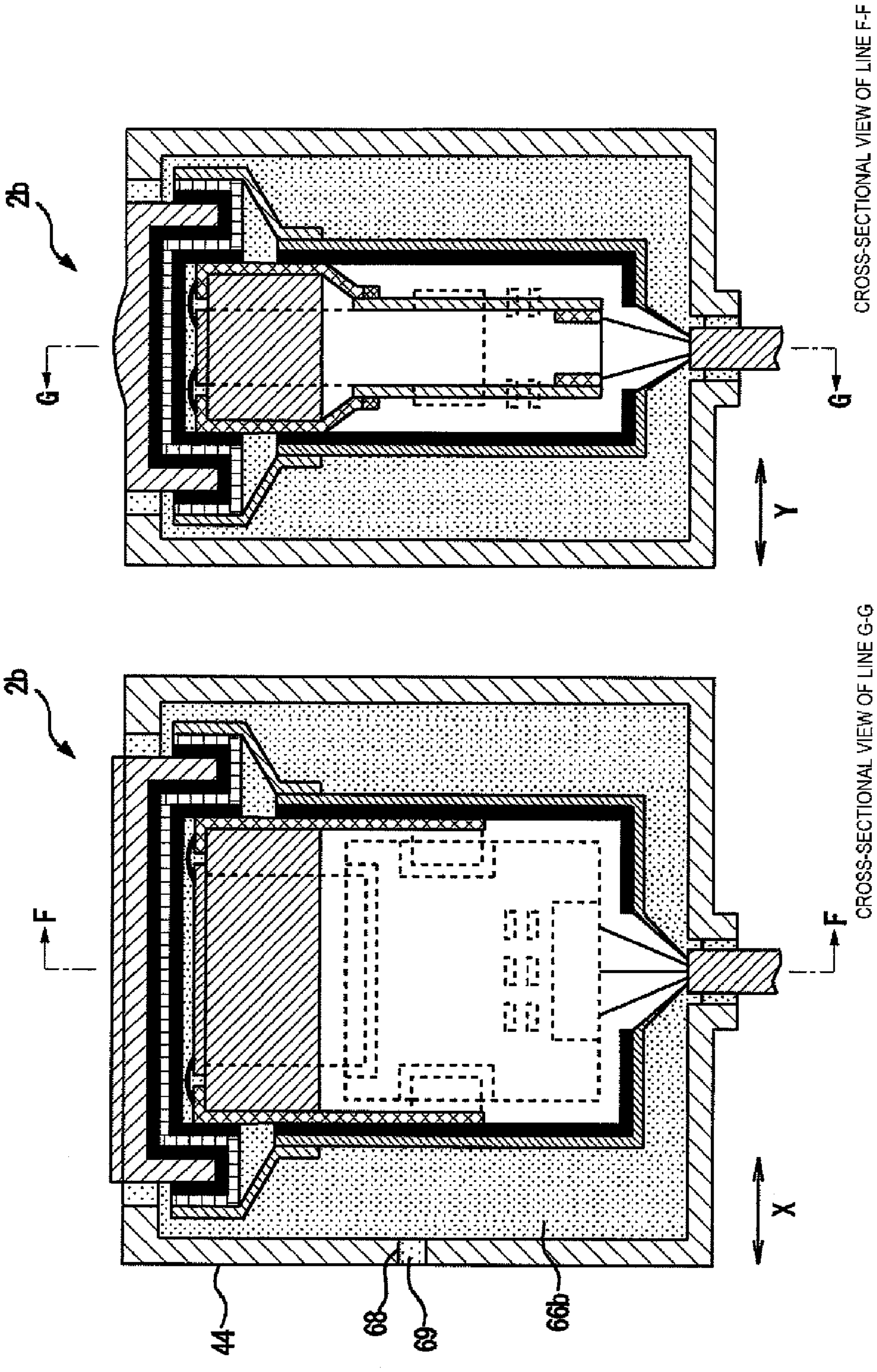
FIG. 10 is a view showing an ultrasonic probe 2*b* according to a third embodiment.

FIG. 10 is a view showing an ultrasonic probe 2*b* according to the third embodiment. FIG. 10(*a*) is a cross-sectional view of a long-axis direction X. FIG. 10(*b*) is a cross-sectional view of a short-axis direction Y. FIG. 10(*a*) is a cross-sectional view of line G-G of FIG. 10(*b*), and FIG. 10(*b*) is a cross-sectional view of line F-F of FIG. 10(*a*). FIG. 10(*b*) corresponds to a cross-sectional view of a plane A of the ultrasonic probe 2 of FIG. 2.

Although the charging material 66 is filled between the acoustic lens 26 and the case 25 in the first embodiment, a filler 66*b* is filled in an overall space of the case 25 in the third embodiment.

An inlet 68 is provided in the case 25 in advance. The filler 66*b* is injected from the inlet 68 into the overall internal space of the case 25 after assembling the ultrasonic probe 2*b*. After injecting the filler 66*b*, the inlet 68 is sealed by a sealant 69. In addition, an airtight cover may be provided on the inlet 68.

In the ultrasonic probe 2*b* of the third embodiment, since the filler 66*b* is filled in the overall internal space of the case 25, it is possible to prevent corrosion of the internal constituent member. It is possible to improve impact resistance or insulating property and to improve safety of the ultrasonic probe 2*b*. In addition, it is possible to prevent deformation of the case 25 or to reduce the weight thereof.

It is preferable that the material of the filler 66*b* has a light weight, an impact resistance or an insulating property. For example, silicon-based resin may be used as the filler 66*b*.

(6. Fourth Embodiment)

Next, a fourth embodiment will be described with reference to FIG. 11.

Figure 11:
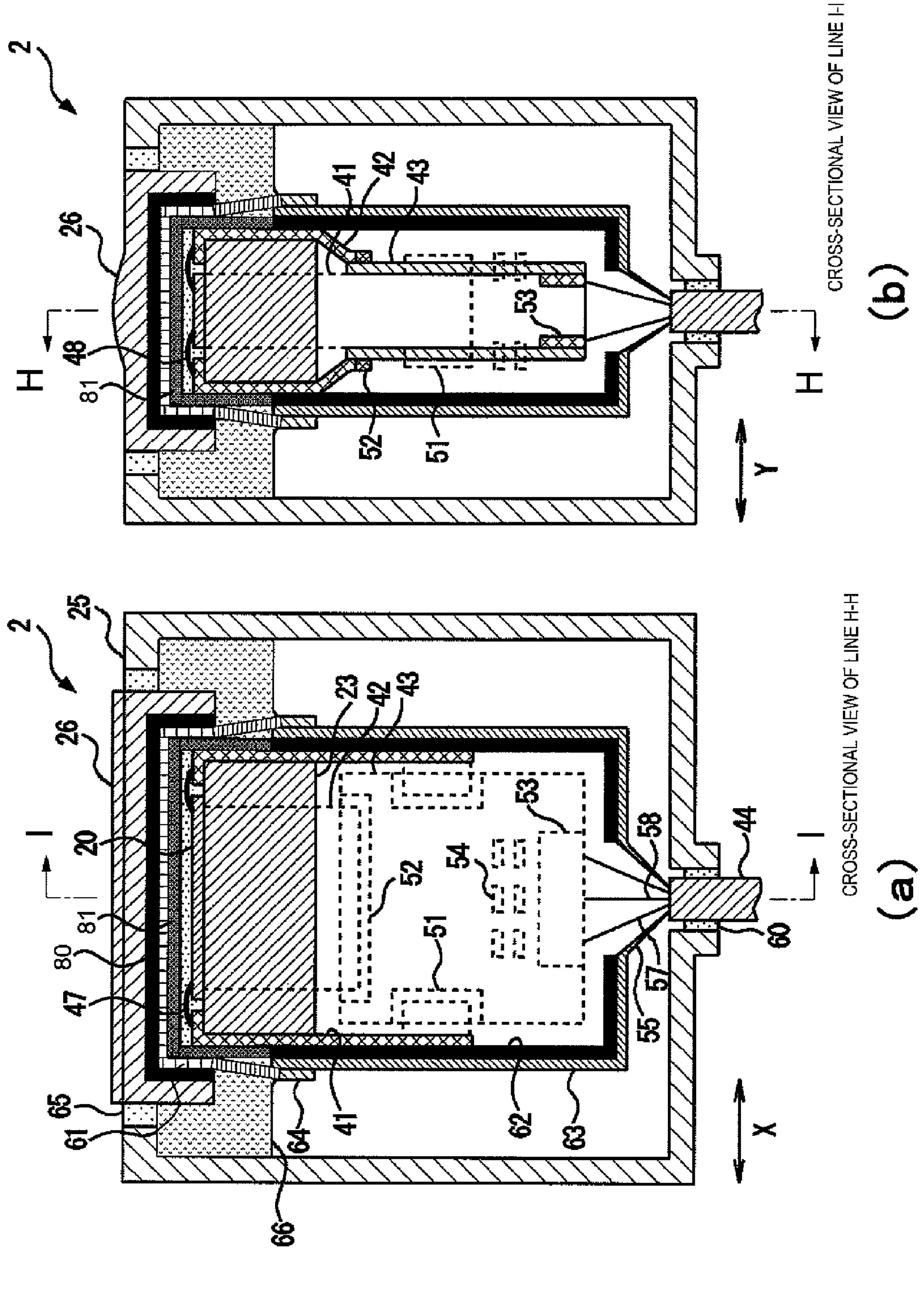
FIG. 11 is a view showing an ultrasonic probe 2*c* according to a fourth embodiment.

FIG. 11 is a view showing an ultrasonic probe 2*c* according to the fourth embodiment. FIG. 11(*a*) is a cross-sectional view of a long-axis direction X. FIG. 11(*b*) is a cross-sectional view of a short-axis direction Y. FIG. 11(*a*) is a cross-sectional view of line H-H of FIG. 11(*b*), and FIG. 11(*b*) is a cross-sectional view of line I-I of FIG. 11(*a*). FIG. 11(*b*) corresponds to a cross-sectional view of a plane A of the ultrasonic probe 2 of FIG. 2.

Although the insulating layer is included between the electrical wiring portion, the mounting board and the casing portion in the first embodiment, an insulating layer is provided so as to cover the overall periphery of the electrical wiring portion and the mounting board in the fourth embodiment.

An insulating film 80 and the conductive film 61 are formed on the inner surface (concave portion) of the acoustic lens 26. In detail, the insulating film 80 is deposited along the inner surface of the acoustic lens 26. In addition, the conductive film 61 is deposited on the deposited insulating film 80. The conductive film 61 is, for example, a Cu film. In addition, two insulating films 80 may be formed with the conductive film 61 interposed therebetween.

An insulating film 81 is adhered to the ultrasonic transmission/reception surface of the cMUT chip 20 through an adhesive. In addition, the insulating film 81 may be deposited on the cMUT chip 20. The insulating film 81 is formed of a material which scarcely influences ultrasonic transmission/reception, such as a silicon oxide or paraxylylene insulating film.

The insulating film 81 adhered to the ultrasonic transmission/reception surface of the cMUT chip 20 covers the wire 47 and the wire 48 for connecting the cMUT chip 20 and the FPC 41, and the FPC 41 on the ultrasonic transmission/reception surface. In addition, the insulating film 81 covers the FPC 41 bent downward from the ultrasonic transmission/reception surface. That is, the insulating film 81 is formed so as to cover the periphery such as the cMUT chip 20 and the FPC 41.

The insulating film 81 is connected to the insulating member 62 on the FPC 41. The insulating member 62 is a member having an insulating property. The insulating member 62 is, for example, an insulating tape formed of silicon oxide or paraxylylene. The insulating member 62 covers the FPC 41 bent downward from the ultrasonic transmission/reception surface of the FPC 41. In addition, the insulating member 62 covers the mounting board 43, on which the electrical parts 54 such as a resistor or a capacitor are mounted, from the side to the bottom thereof.

The conductive film 61 and the conductive member 63 are connected through the conductive member 64. The conductive member 63 and the conductive member 64 are high-reliable high-rigidity conductive members which are hard to damage compared with the conductive film 61. The conductive member 63 and the conductive member 64 are, for example, Cu tapes. The conductive member 64 is fixed to the conductive film 61 of the inner side surface of the acoustic lens 26 and the conductive member 63 provided on the outer surface of the insulating member 62.

The conductive member 63 is connected to the coaxial cable 55 (shield line). The coaxial cable 55, the coaxial cable 57 and the coaxial cable 58 are bundled through the cable 44 so as to be connected to the body of the ultrasonic diagnosis device 1.

The case 25 is provided on the four side surfaces of the ultrasonic probe 2. The case 25 is fixed to the four side surfaces of the acoustic lens 26. The operator grasps the case 25 and operates the ultrasonic probe 2. A sealant 65 is filled in a gap between the case 25 and the acoustic lens 26. A sealant 60 is filled in a gap between the case 25 and the cable 44. In addition, a filling material 66 is filled between the acoustic lens 26 and the case 25.

In addition, it is preferable that the upper end of the case 25 is located above the cMUT chip 20. Accordingly, even when an unexpected state such as falling of the ultrasonic probe 2 occurs, it is possible to prevent direct impact so as to protect the cMUT chip 20.

(7. Others)

With respect to a method of forming the conductive film or the insulating film, there is a method of forming the case 25, the acoustic lens 26 and in-molding an insulating sheet having a conductive film attached thereto at the same time or a method of forming the insulating film or the conductive film by physical deposition or chemical deposition. It is preferable that the film thickness of the conductive layer is about 0.1 μm and the film thickness of the insulating layer is about 1 μm. By thinning the film thickness of the insulating layer and the conductive layer, it is possible to suppress influence on the ultrasonic wave transmitted/received in the cMUT chip (influence on pulse/frequency characteristics or attenuation).

Although the suitable embodiments of the ultrasonic probe and the ultrasonic diagnosis device according to the present invention are described with reference to the accompanying drawings, the present invention is not limited to the examples. It is understood by those skilled in the art that various modifications or alterations are made in the technical range disclosed in the present invention and are included in the technical range of the present invention.

The invention claimed is:

1. An ultrasonic probe comprising:
- a Capacitive Micromachined Ultrasonic Transducer (cMUT) chip having a plurality of vibration elements to transmit or receive an ultrasonic wave;
- a mounting board on which electrical parts for controlling the vibration elements are mounted;
- an electrical wiring portion to connect the mounting board and the cMUT chip;
- a casing portion for storing the cMUT chip, the mounting board and the electrical wiring portion; and
- an acoustic lens for converging the ultrasonic wave from the cMUT chip;
- wherein an insulating portion is provided between the mounting board and the casing portion;
- wherein the cMUT chip, the electrical wiring portion and the mounting board are stored in a closed space formed by a conductive film and a ground layer having a ground potential;
- wherein a part of the ground layer is provided along an ultrasonic wave radiation side of the cMUT chip and is provided along a backward side of the acoustic lens.

2. The ultrasonic probe according to claim 1, wherein the insulating portion is provided along a surface of the electrical wiring portion.

3. The ultrasonic probe according to claim 1, wherein the insulating portion is provided so as to cover the overall periphery of the mounting board.

4. The ultrasonic probe according to claim 1, wherein the insulating portion is provided along an inner surface of the casing portion.

5. The ultrasonic probe according to claim 1, wherein the insulating portion includes an insulating member of silicon oxide or paraxylylene.

6. The ultrasonic probe according to claim 1, wherein the ground layer is provided along an ultrasonic wave radiation side of the cMUT chip and a surface of the electrical wiring portion or an inner surface of the casing portion.

7. The ultrasonic probe according to claim 1, wherein the ground layer includes a conductive member.

8. The ultrasonic probe according to claim 1, wherein the ground layer is provided along the outer surface of the insulating layer.

9. The ultrasonic probe according to claim 1, wherein a filler is filled in at least a portion of an internal space of the casing portion.

10. The ultrasonic probe according to claim 1, wherein a filler is filled in an overall internal space of the casing portion for storing the cMUT chip.

11. The ultrasonic probe according to claim 1, wherein an acoustic lens is provided on an ultrasonic wave radiation side of the cMUT chip and a backing layer is provided on a side of the cMUT chip opposed to the acoustic lens.

12. The ultrasonic probe according to claim 11, wherein the electrical wiring portion is placed along the backing layer.

13. The ultrasonic probe according to claim 11, wherein the insulating portion is provided between the cMUT chip and the acoustic lens.

* * * * *